United States Patent
Hart et al.

(10) Patent No.: US 7,326,233 B2
(45) Date of Patent: Feb. 5, 2008

(54) SURGICAL CLIP

(75) Inventors: Charles C. Hart, Summerville, SC (US); Said Hilal, Coto de Caza, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 423 days.

(21) Appl. No.: 10/935,967

(22) Filed: Sep. 8, 2004

(65) Prior Publication Data

US 2005/0038459 A1 Feb. 17, 2005

Related U.S. Application Data

(62) Division of application No. 10/052,329, filed on Jan. 18, 2002, now Pat. No. 6,818,009.

(60) Provisional application No. 60/151,496, filed on Aug. 30, 1999.

(51) Int. Cl.
*A61B 17/04* (2006.01)
*A61B 17/08* (2006.01)

(52) U.S. Cl. .................. 606/232; 606/151; 606/157

(58) Field of Classification Search .............. 606/139, 606/151, 157, 228–232, 142
See application file for complete search history.

(56) References Cited

U.S. PATENT DOCUMENTS

| | | | |
|---|---|---|---|
| 3,753,438 A * | 8/1973 | Wood et al. | 606/232 |
| 4,055,874 A | 11/1977 | Brown | |
| 5,179,765 A | 1/1993 | Sungberg | |
| 5,279,416 A * | 1/1994 | Malec et al. | 206/339 |
| 5,352,371 A | 10/1994 | Felt | |
| 5,441,509 A | 8/1995 | Vidal et al. | |
| 5,474,572 A | 12/1995 | Hayhurst | |
| 5,665,109 A * | 9/1997 | Yoon | 606/232 |
| 5,669,917 A | 9/1997 | Sauer et al. | |
| 5,824,008 A * | 10/1998 | Bolduc et al. | 606/143 |
| 5,875,602 A | 3/1999 | Lappin et al. | |
| 6,015,417 A | 1/2000 | Reynolds, Jr. | |
| 2002/0173805 A1 | 11/2002 | Matsuno et al. | |
| 2003/0093091 A1 | 5/2003 | Paolitto et al. | |

FOREIGN PATENT DOCUMENTS

DE    299 13 246 U1    9/1999
EP    1 072 225 A3     1/2001

OTHER PUBLICATIONS

European Patent Office, Supplementary Partial European Search Report for Application EP 00974062.2, dated Apr. 13, 2006.

* cited by examiner

*Primary Examiner*—Glenn K. Dawson
*Assistant Examiner*—Kathleen Sonnett
(74) *Attorney, Agent, or Firm*—Patrick Y. Ikehara; Kenneth K. Vu

(57) ABSTRACT

A surgical clip having a sliding state and a crimped state is adapted for use in a surgical procedure initially to slide along suture ends to an operative position and ultimately to crimp the suture ends at the operative position. a sub straight, bendable between the sliding state and the crimped state carries at least one coating having either lubricious or traction enhancing properties. A second coating can be added to form a coating laminate with the outer coating having lubricious properties facilitating the sliding state and the inner coating having traction enhancing properties facilitating thee crimped state.

7 Claims, 7 Drawing Sheets

SURGICAL CLIP

CROSS REFERENCE TO RELATED APPLICATIONS

This application is a divisional of U.S. patent application Ser. No. 10/052,329, filed on Jan. 18, 2002, now U.S. Pat. No. 6,818,009 entitled "Improved Surgical Clip," which claims benefit under 35 U.S.C. 365(c) of PCT/US00/40773, filed Aug. 30, 2000, entitled "Improved Surgical Clip," and under 35 U.S.C. 119(e) of U.S. Provisional Application Ser. No. 60/151,496, filed Aug. 30, 1999, entitled "Suture Clinch with Traction Enhancement," all of which are fully incorporated herein by reference.

BACKGROUND OF THE INVENTION

1. Field of the Invention

This invention relates generally to surgical clips and clamps, and clinches adapted for use with sutures.

2. Discussion of the Prior Art

In the surgical environment, clips and clamps have been used for removably holding two objects in close proximity. These objects may include tissue, vessels or other surgical devices such as sutures. Clips and clamps may be of the variety disclosed and claimed by Applicant in U.S. Provisional Patent Application Ser. No. 60/040,655, filed Mar. 10, 1997, and entitled "Surgical Clips and Clamps". Suture clinches of the past are well represented by Applicant's U.S. patent application Ser. No. 09/082,495, filed May 21, 1995, and entitled "Suture Clinch". Both of these applications are incorporated herein by reference. In the latter application, a metal clinch is disclosed to be stamped from a sheet of metal and pre-formed to operate with an associated clinch applier. The two free ends of a suture are disposed within the clinch, which is then slid down the suture ends and crimped to bind the suture ends in a fixed relationship. As used herein, the word "clip" refers not only to clips, but also to clamps, clinches, and other surgical devices adapted for use in the foregoing methods.

In the case of the metallic clinches of the past, the metal-to-suture interface tends to provide a coefficient of friction that initially is too high to facilitate the sliding step of the process, and ultimately is too low to lock the suture ends in a fixed relationship.

SUMMARY OF THE INVENTION

In accordance with the present invention, a coating is provided on the clip in order to facilitate one or more of the steps in its method of operation. With respect to a suture clip, a coating is contemplated which would initially facilitate the sliding step by providing a reduced coefficient of friction with the suture ends. Another type of coating might provide an increased coefficient of friction with the suture ends, thereby facilitating traction enhancement during the locking step. More than one layer of material may be included in the coating, to facilitate both the initial stage as well as the ultimate stage of operation.

Any coating applied to a suture clinch would tend to function as an occlusive cushion to inhibit abrasion between sharp edges and corners of the clinch, and the suture material. For traction enhancement, any material can be used as a coating to produce an increased coefficient of friction with the suture material. In a preferred embodiment, the material chosen is identical to that of the suture material, since similar or identical materials normally exhibit increased frictional resistance to slipping. A more compliant material might be chosen for the traction enhancement coating in order to increase the area of contact between the clinch and the suture. By increasing the area of contact, elevated compressive pressures need not be applied to securely hold the suture.

The traction enhancement coating might also be selected to enhance the holding ability with a resorbable suture. This permits those portions of the suture distant from the clinch to be resorbed, while the suture in the clinch is protected from the resorption process. In preferred embodiments, the traction-enhancing coating includes plastics such as polypropylene or polyethylene.

A lubricious coating could be applied to facilitate the sliding of the clinch along the suture ends. In this case, a reduced coefficient of friction is desirable. A coating of hydrophilic or hydrophilic-hydrophobic material is contemplated to provide the desired lubricity. In a further embodiment, the clinch is coated with two layers of material in a laminate. The first layer is coated on the metallic clinch to provide traction enhancement. The second layer is coated on the first layer. Initially, the second layer contacts the suture and provides the desired lubricity for sliding the clinch into place. With a hydrophilic coating, moisture is attracted to provide the desired lubricity. As the second layer is oblated by movement of the suture during the sliding step, the first substrate is exposed and ultimately compressed against the suture in the locking step. Alternatively, the second layer may be displaced by the compression of the clinch upon the suture. In either case, once the clinch is operatively disposed in its desired position, the first traction-enhancing coating engages the suture ends to lock the suture.

The coatings can be applied in accordance with any known method for coating objects. Dip-coating is initially contemplated, but dispersions, solid castings, insert moldings, and spraying may also be appropriate. The coatings can be separately formed and adhered to the metallic base in a further process. Typically, the laminate or coating will be applied to the clinch while it is in a flat-formed condition.

These and other features and advantages of the invention will be better understood with reference to certain preferred embodiments and the best mode of the invention, taken in combination with the associated drawings.

DESCRIPTION OF THE DRAWINGS

FIG. 1 is a perspective view showing the clip initially applied to suture ends to facilitate closure of a tissue wound;

FIG. 2 is a perspective view showing the step of sliding the surgical clip along the suture ends;

FIG. 3 is a perspective view illustrating the step of crimping the suture clip at an operative position;

FIG. 4 is a perspective view showing the step of cutting the suture ends leading the crimped surgical clip to maintain the suture ends in a fixed relationship;

DESCRIPTION OF PREFERRED EMBODIMENTS AND BEST MODE OF THE INVENTION

Figure 1:
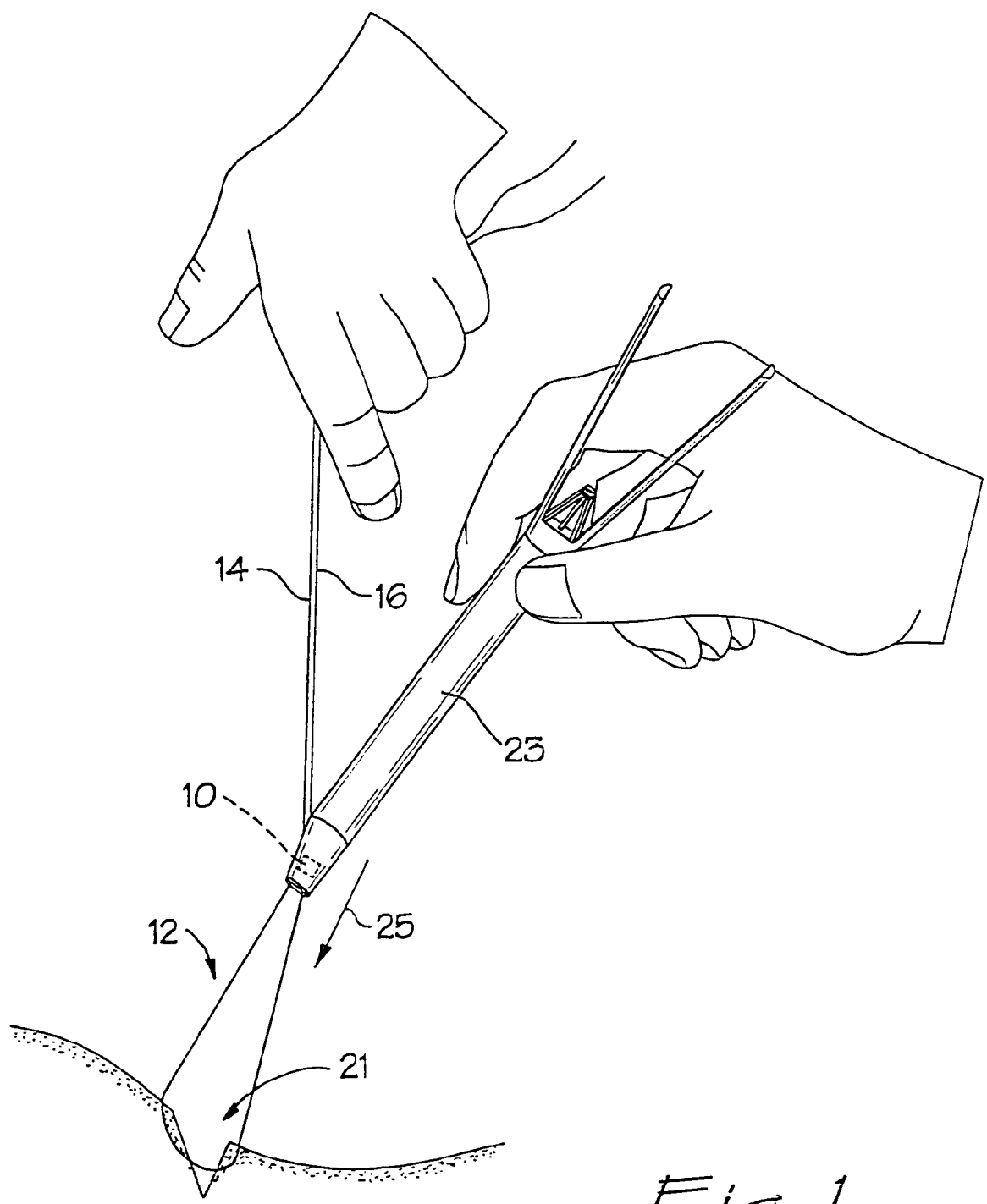
FIGS. 1-4 illustrate progressive steps in a method associated with the surgical clip of the present invention.

A surgical clip is illustrated in FIG. 1 and designated generally by the reference numeral 10. The clip 10 is representative not only of surgical clips, but also clamps, clinches, and other surgical devices adapted for application to tissue, vessels, and other body conduits, as well as other surgical devices such as a suture 12, illustrated in FIG. 1.

The suture 12 includes suture ends 14 and 16 that are sewn through adjacent portions of tissue 18, which define a wound 21. In this operation, the suture ends 14 and 16 are typically held by one hand of the surgeon, while a clip applier 23 is used to apply the clip 10 to the suture ends 14, 16.

Figure 2:
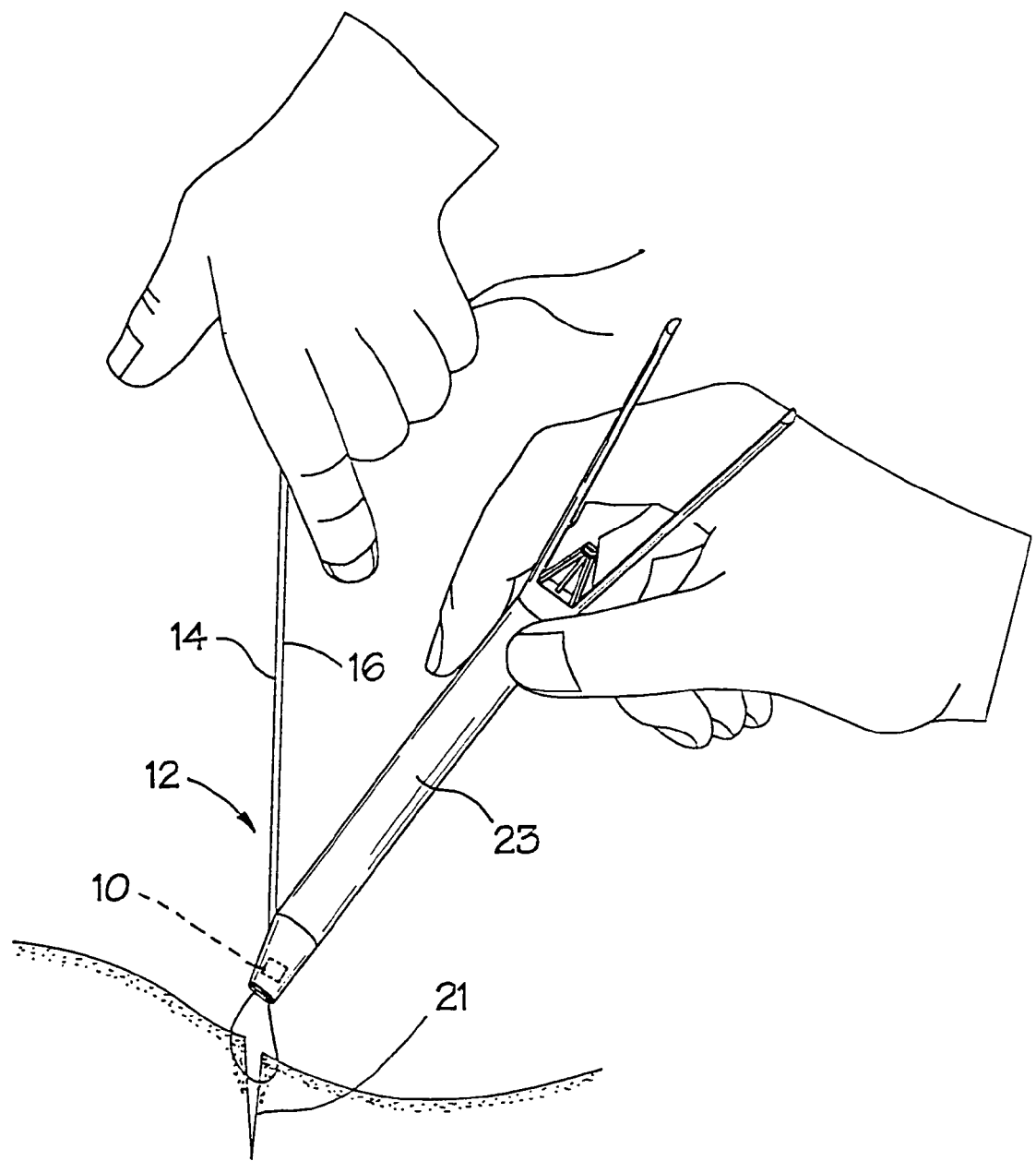

The clip applier 23 is adapted to move the clip 10 between an initial sliding state and an ultimate crimped state. When the clip 10 is initially applied to the suture ends 14, 16, as illustrated in FIG. 1, it is in the sliding state. After the clip 10 has been applied to the suture ends 14, 16, it can be slid downwardly on the suture 12, as illustrated by an arrow 25. This sliding step will ultimately bring the clip 10 to an operative position, as illustrated in FIG. 2. In this operative position, the clip 10 is maintained in proximity to the tissue 18 where it draws the suture ends 14,16 taught, thereby closing the wound 21.

Figure 3:
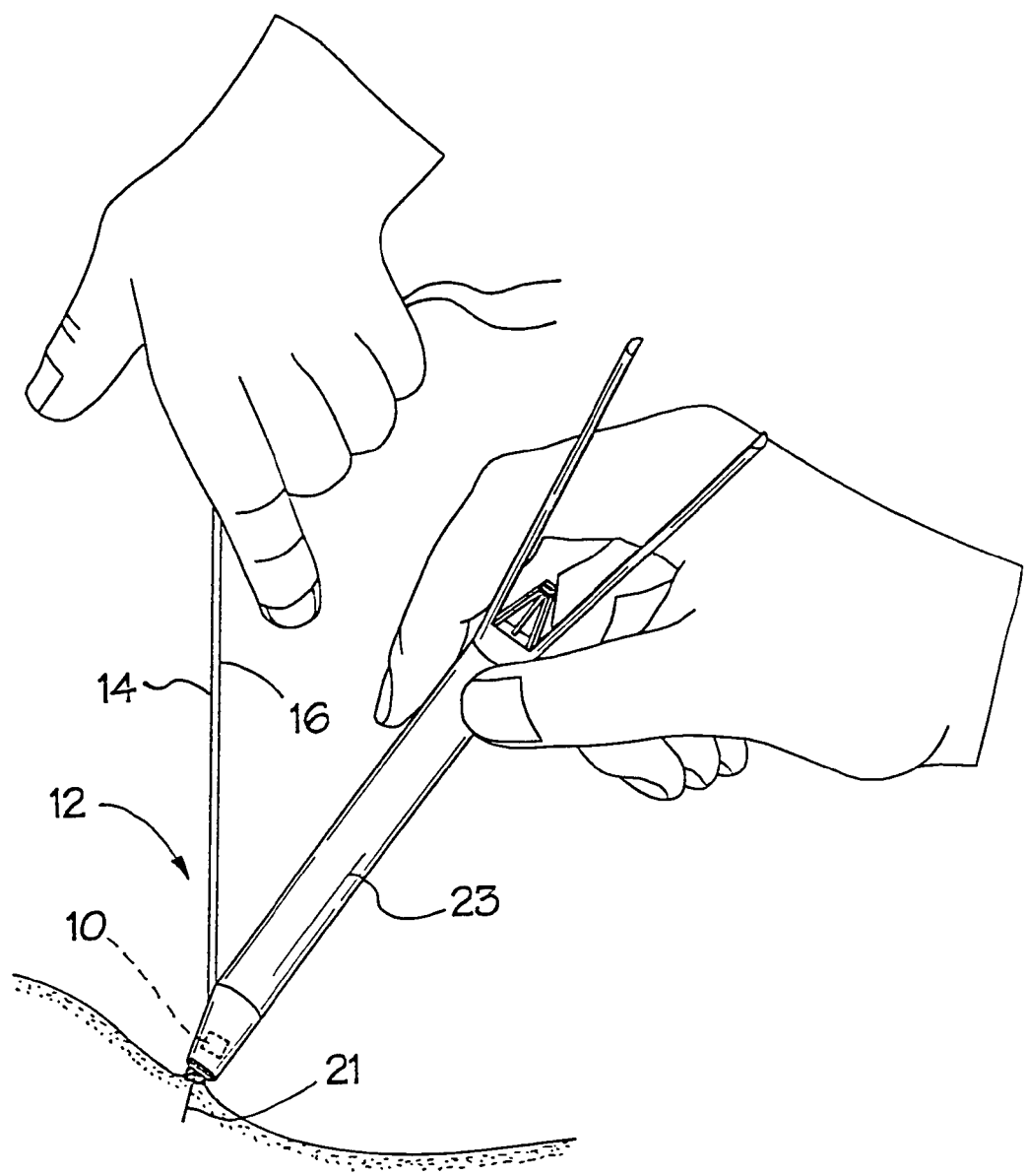
Figure 4:
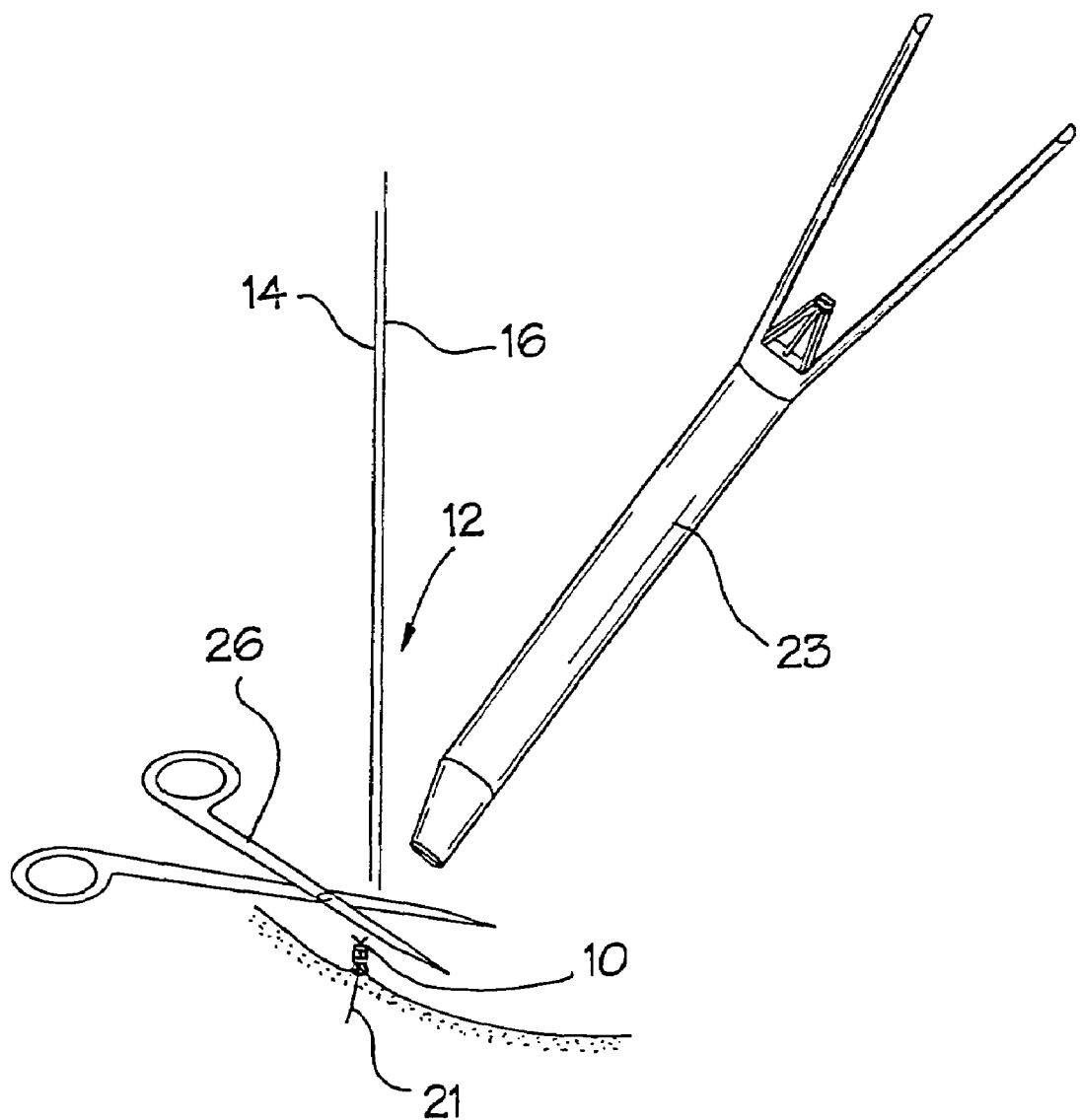

In this operative position, the clip applier 23 can be operated to move the clip 10 from its sliding state to its crimped or locked state, as illustrated in FIG. 3. In the crimped state, the clip 10 tightly engages the suture ends 14 and 16, locking the suture 12 so that the wound 21 is maintained in a closed state. As shown in FIG. 4, the suture ends 14 and 16 can ultimately be cut, for example, with scissors 26, and the clip applier 23 removed from the operative site.

Figure 5:
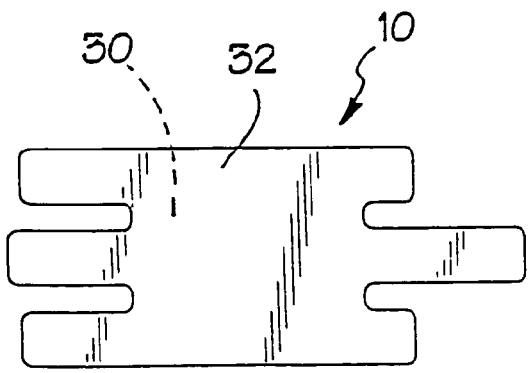
FIG. 5 is a top-plan view of a preferred embodiment of the surgical clip adapted for use in the foregoing method.

In order to facilitate this operation, the clip of the present invention, illustrated in the plan view of FIG. 5, can be provided with a substrate 30 and a coating 32 carried by the substrate 30. The substrate 30 is preferably formed of a material having some rigidity, but also being bendable between the sliding state and the crimped state. The yield point of the material should also be sufficiently high that the clip 10 can be maintained in these respective states. In a preferred embodiment the substrate is formed of a metal, such as stainless steel, having a first coefficient of friction with the substrate 12.

Figure 6:
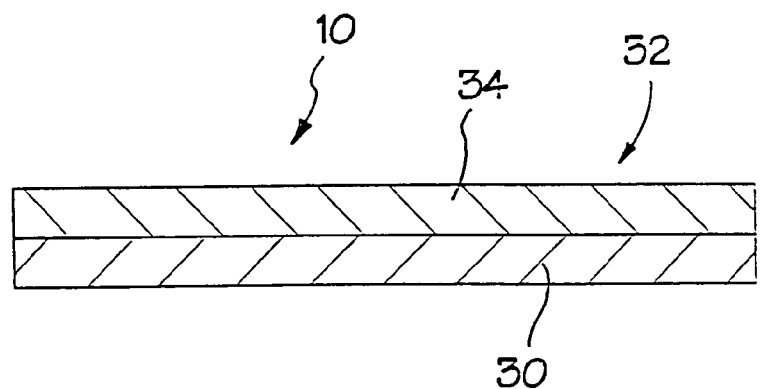
FIG. 6 is a side-elevation view showing the suture clip of FIG. 5 with a lubricious coating.

The coating 32 may include a single layer of material or multiple layers forming a laminate, as discussed in greater detail below. If only a single layer is contemplated for the coating 32, various characteristics for the material forming the coating 32 can be chosen in order to facilitate the foregoing process. For example, as illustrated in FIG. 6, the coating 32 can include a single layer 34 having lubricious properties. As the clip 10 is applied to the suture ends 14, 16, this layer 34 will contact the suture 12 and provide a second coefficient of friction with the suture 12 that is less than the first coefficient of friction associated with the substrate 30. By way of example, the material forming the lubricious layer 34 can be hydrophilic or hydrophobic. In a preferred embodiment, fluorinated polymers and oils are contemplated for the lubricious layer 34.

Figure 7:
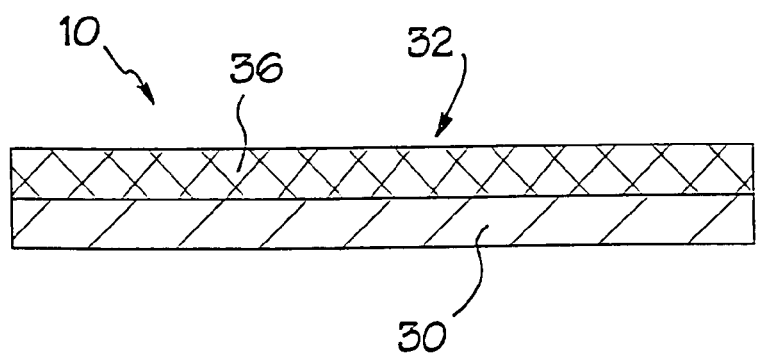
FIG. 7 is a side-elevation view showing the surgical clip of FIG. 5 with a traction-enhancing coating.
Figure 8:
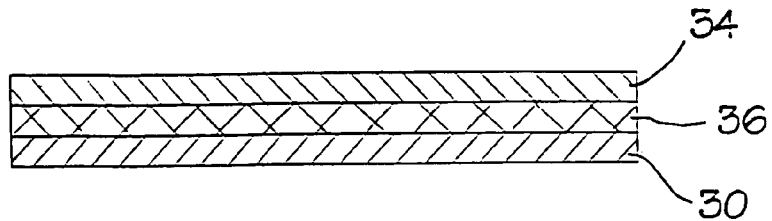
FIG. 8 is a side-elevation view of the surgical of FIG. 5 and illustrating an embodiment having a coating, including both the layer of lubricious material and the layer of traction-enhancing material.

Alternatively, the coating 32 can be formed of a single layer 36 carried by the substrate 30, as illustrated in FIG. 7. In this construction, the layer 36 is preferably made from a traction-enhancing material having a third coefficient of friction with the suture 12 which is greater than the first coefficient of friction associated with the substrate 30. With these characteristics, the layer 36 of the coating 32 has increased traction characteristics greatly facilitating a fixed relationship with the suture ends 14, 16 when the clip 10 is in the crimped state, as illustrated in FIG. 3. In certain preferred embodiments, the traction-enhancing layer 36 includes plastic materials such as polypropylene and polyethylene.

The material forming the traction-enhancing layer 36 may advantageously be chosen with compliant characteristics, which increase the area of contact between the clip 10 and the suture 12. Traction enhancement may also be facilitated by forming the layer 36 of a material which includes the material of the suture 12. For example, if the suture 12 is formed of polyethylene, it may be desirable to form the layer 36 of the same polyethylene material in order to increase frictional resistance.

Figure 9:
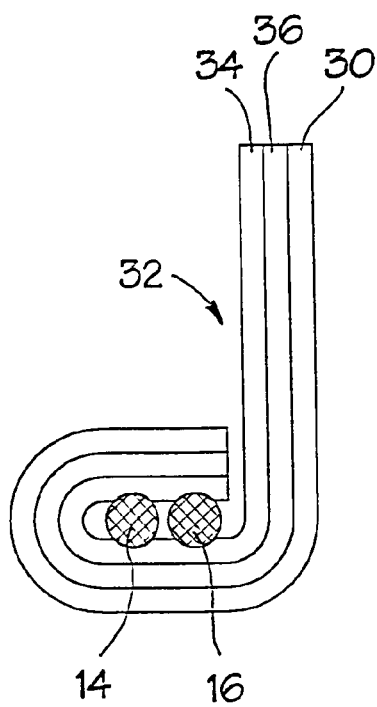
FIG. 9 is a radial cross-section view of the clip engaging suture ends in the sliding state illustrated in FIG. 1.

In still another embodiment of the clip 10, the coating 32 is formed as a laminate, which includes both the lubricious layer 34 and the traction-enhancing layer 36. It will be noted that in this construction, the traction-enhancing layer 36 is disposed between the lubricious layer 34 and the substrate 30. Referring to the method steps illustrated in FIGS. 1-4, the advantages of this laminate construction will be particularly apparent. Initially, when the clip 10 is applied to the suture ends 14, 16, as illustrated in FIG. 1, the suture 12 engages only the lubricious layer 34, as illustrated in FIG. 9. With the characteristics provided by the material of this layer 34, the clip 10 can be more easily slid to its operative position, as illustrated in FIG. 2.

Figure 10:
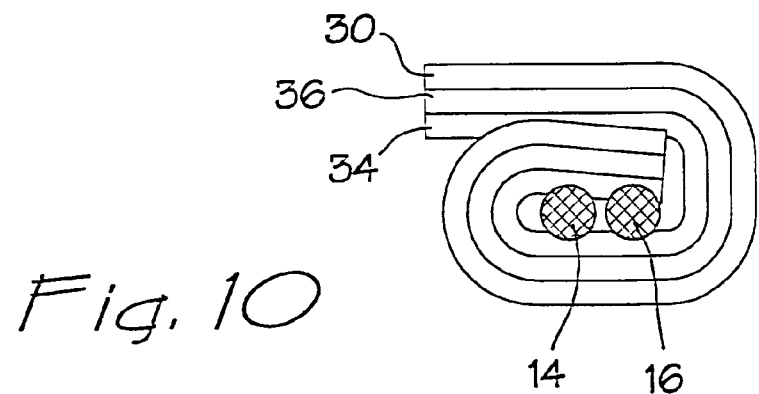
FIG. 10 is a radial cross-section view of the clip engaging the suture ends in the crimped state illustrated in FIG. 3.

When the clip 10 is moved to its crimped state, as illustrated in FIG. 3, the suture ends 14 and 16 penetrate the lubricious layer 34 to contact the traction-enhancing layer 36. This penetration and contact is illustrated in FIG. 10, where the increased coefficient of friction provided by the traction-enhancing layer 36 aids in maintaining the suture ends 14 and 16 in a locked state at the operative site.

From the foregoing discussion, it will be apparent that surgical devices used in performing steps in the methods, such as sliding and locking, can be provided with coatings having properties that facilitate those steps of an operation. Particularly where the operation is performed with respect to non-tissue components, such as sutures, the materials of those devices should also be considered in choosing lubricious or traction-enhancing characteristics for the coating layers.

Figure 11:
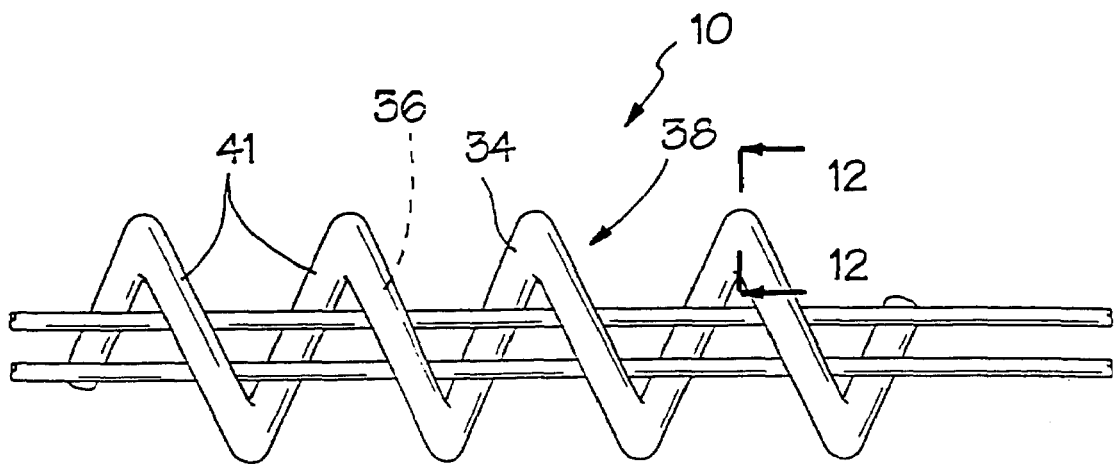
FIG. 11 is a side elevation view of a clip having the configuration of a spring with convulsions.
Figure 12:
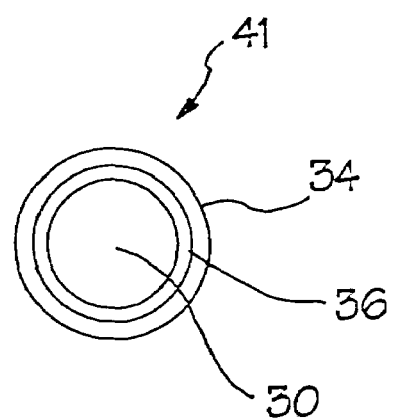
FIG. 12 is a cross section view taken along lines 12-12 of FIG. 11 and illustrating coatings on the convulsions of the spring.

It will be apparent that this concept of applying at least one coating to a surgical clip such as a suture clinch, is applicable to any clip regardless of the configuration of its substrate. By way of example, it will be noted with reference to FIG. 11 that such a coating could be applied to a clip in the form of a coil or spring 38 having convulsions 41. In this case, the coating would typically surround each of the convulsions 41, for example as illustrated in the cross section view of FIG. 12. In this view, the laminate 32 includes both the traction enhancing coating 36 and the lubricious coating 34.

Given the many modifications, which will now be apparent for both the foregoing apparatus and method, one is cautioned not to restrict the inventive concept to the preferred embodiments and methods discussed, but rather to determine the scope of the invention only with reference to the following claims.

The invention claimed is:

1. A surgical combination, including:
   a pair of suture ends formed of a first material;
   a clip having a sliding state facilitating a sliding relationship with the suture ends to an operative position, and a crimped state facilitating a fixed relationship with the suture ends at the operative position;
   a coating forming a barrier to inhibit contact between the suture ends and the clip and a second coefficient of friction associated with the coating is less than a first coefficient of friction associated with the clip in order to facilitate the sliding relationship between the suture ends and the clip in the sliding state;
   wherein the coating is a first layer and the coating further comprises:
   a second layer having a third coefficient of friction associated with the second layer, the third coefficient of friction being greater than both the first coefficient of friction associated with the clip and the second coefficient of friction associated with the first layer.

2. The surgical combination recited in claim 1 wherein the second layer is disposed between the first layer and the clip.

3. The surgical combination recited in claim 1 wherein the first material of the suture ends is resorbable.

4. A method for applying a surgical clip to a pair of suture ends formed of a first material, the method comprising the steps of:
   providing the surgical clip with a substrate having a first coefficient of friction with the first material of the suture ends and a coating on the substrate, the coating including a first layer of a third material carried by the substrate, the first layer having a second coefficient of friction with the first material greater than the first coefficient of friction, and a second layer carried by the first layer, the second layer having a third coefficient of friction with the first material of the suture ends less than the second coefficient of friction associated with the first layer;
   sliding the clip along the suture ends to an operative position;
   during the sliding step, contacting the suture ends with the second layer of the coating to facilitate the sliding step with the lesser third coefficient of friction;
   moving the substrate relative to the suture ends to maintain the suture ends in a fixed relationship at the operative site; and
   during the moving step, contacting the suture ends with the first layer of the coating to facilitate the fixed relationship with the greater second coefficient of friction.

5. The method recited in claim 4 wherein the moving step includes the step of bending the substrate relative to the suture ends.

6. The method recited in claim 5 wherein the bending step includes the step of crimping the surgical clip around the suture ends at the operative site.

7. The method recited in claim 4 wherein, prior to the end of the bending step, the method further comprises the step of:
   penetrating the second layer of the coating with the suture ends to bring the suture ends in to contact with the first layer of the coating.

* * * * *